(12) United States Patent
Eidenschink et al.

(10) Patent No.: US 12,296,114 B2
(45) Date of Patent: *May 13, 2025

(54) DELIVERY CATHETER SYSTEMS AND METHODS

(71) Applicant: Pacesetter, Inc., Sylmar, CA (US)

(72) Inventors: Tracee Eidenschink, Wayzata, MN (US); Thomas B. Eby, Mountain View, CA (US); Matt Glimsdale, St. Michael, MN (US); Brian J. Perszyk, Shoreview, MN (US)

(73) Assignee: PACESETTER, INC., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/369,779

(22) Filed: Sep. 18, 2023

(65) Prior Publication Data

US 2024/0001078 A1   Jan. 4, 2024

Related U.S. Application Data

(60) Continuation of application No. 16/846,158, filed on Apr. 10, 2020, now Pat. No. 11,779,731, which is a
(Continued)

(51) Int. Cl.
*A61M 25/00* (2006.01)
*A61N 1/05* (2006.01)
(Continued)

(52) U.S. Cl.
CPC ........ *A61M 25/008* (2013.01); *A61M 25/001* (2013.01); *A61N 1/056* (2013.01);
(Continued)

(58) Field of Classification Search
CPC ............ A61M 25/0009; A61M 25/001; A61M 25/008; A61N 1/3756; A61N 1/056;
(Continued)

(56) References Cited

U.S. PATENT DOCUMENTS 5,846,251 A    12/1998  Hart
5,951,495 A     9/1999  Berg et al.
(Continued)

FOREIGN PATENT DOCUMENTS

WO    2007/047681 A2    4/2007

*Primary Examiner* — Robert A Lynch
*Assistant Examiner* — Christina C Lauer
(74) *Attorney, Agent, or Firm* — WOMBLE BOND DICKINSON (US) LLP

(57) ABSTRACT

Disclosed herein is a delivery catheter for implanting a leadless biostimulator. The delivery catheter includes a shaft and a tubular body having a lumen and an atraumatic end. The atraumatic end includes at least one of a braided, woven or mesh construction configured to facilitate the atraumatic end changing diameter. When a distal portion of the shaft is coupled to a proximal region of the leadless biostimulator, at least one of distally displacing the tubular body relative to the shaft or proximally displacing the shaft relative to the tubular body causes the leadless biostimulator to be received in the volume of the atraumatic end and the atraumatic end to encompass the leadless biostimulator. Conversely, at least one of proximally displacing the tubular body relative to the shaft or distally displacing the shaft relative to the tubular body causes the leadless biostimulator to exit the volume of the atraumatic end.

14 Claims, 23 Drawing Sheets

Related U.S. Application Data division of application No. 14/508,556, filed on Oct. 7, 2014, now Pat. No. 10,653,859.

(51) Int. Cl.
*A61N 1/375* (2006.01)
*A61M 25/06* (2006.01)

(52) U.S. Cl.
CPC ........... *A61N 1/059* (2013.01); *A61N 1/3756* (2013.01); *A61M 25/0009* (2013.01); *A61M 2025/0024* (2013.01); *A61M 2025/0081* (2013.01); *A61M 2025/0681* (2013.01); *A61M 2205/0266* (2013.01); *A61M 2207/00* (2013.01)

(58) Field of Classification Search
CPC ......... A61N 1/372–37205; A61B 2017/06185; A61B 17/06166; A61B 2017/00526; A61F 2002/30235; A61F 2002/30688; A61F 2002/5093
See application file for complete search history.

(56) References Cited

U.S. PATENT DOCUMENTS

| | | | |
|---|---|---|---|
| 6,051,017 A | | 4/2000 | Loeb et al. |
| 6,171,297 B1 | | 1/2001 | Pedersen et al. |
| 6,994,677 B1 * | | 2/2006 | Buehlmann .......... A61B 18/148 606/45 |
| 7,270,669 B1 | | 9/2007 | Sra |
| 7,532,933 B2 | | 5/2009 | Hastings et al. |
| 7,627,383 B2 | | 12/2009 | Haller et al. |
| 7,840,281 B2 | | 11/2010 | Kveen et al. |
| 7,937,148 B2 | | 5/2011 | Jacobson |
| 7,945,333 B2 | | 5/2011 | Jacobson |
| 8,010,209 B2 | | 8/2011 | Jacobson |
| 8,185,213 B2 | | 5/2012 | Kveen et al. |
| 8,332,036 B2 | | 12/2012 | Hastings et al. |
| 8,352,025 B2 | | 1/2013 | Jacobson |
| 8,364,280 B2 | | 1/2013 | Marnfeldt et al. |
| 8,457,742 B2 | | 6/2013 | Jacobson |
| 8,527,068 B2 | | 9/2013 | Ostroff |
| 8,615,310 B2 | | 12/2013 | Khairkhahan et al. |
| 8,855,789 B2 | | 10/2014 | Jacobson |
| 9,205,225 B2 | | 12/2015 | Khairkhahan et al. |
| 10,653,859 B2 * | | 5/2020 | Eidenschink .......... A61N 1/056 |
| 2001/0044595 A1 * | | 11/2001 | Reydel .............. A61M 25/0668 604/523 |
| 2001/0051790 A1 * | | 12/2001 | Parker ................. A61M 25/005 604/524 |
| 2003/0199818 A1 | | 10/2003 | Waldhauser et al. |
| 2004/0116848 A1 | | 6/2004 | Gardeski et al. |
| 2004/0116955 A1 * | | 6/2004 | Foltz .................... A61M 31/00 606/193 |
| 2005/0021002 A1 | | 1/2005 | Deckman et al. |
| 2005/0080430 A1 * | | 4/2005 | Wright, Jr. ......... A61B 17/3468 606/108 |
| 2005/0267555 A1 * | | 12/2005 | Marnfeldt .......... A61B 17/3468 607/116 |
| 2005/0288764 A1 | | 12/2005 | Snow et al. |
| 2006/0085039 A1 | | 4/2006 | Hastings et al. |
| 2006/0085041 A1 | | 4/2006 | Hastings et al. |
| 2007/0088396 A1 | | 4/2007 | Jacobson |
| 2007/0088397 A1 | | 4/2007 | Jacobson |
| 2007/0150037 A1 | | 6/2007 | Jastings et al. |
| 2007/0150038 A1 | | 6/2007 | Hastings et al. |
| 2007/0156084 A1 | | 7/2007 | Belhe et al. |
| 2007/0219590 A1 | | 9/2007 | Hastings et al. |
| 2008/0021532 A1 | | 1/2008 | Kveen et al. |
| 2009/0281605 A1 | | 11/2009 | Marnfeldt et al. |
| 2011/0034939 A1 | | 2/2011 | Kveen et al. |
| 2012/0179033 A1 | | 7/2012 | Merhi |
| 2012/0232565 A1 | | 9/2012 | Kveen et al. |
| 2014/0012344 A1 | | 1/2014 | Hastings et al. |
| 2015/0105729 A1 | | 4/2015 | Valeti et al. |

* cited by examiner

FIG. 3A
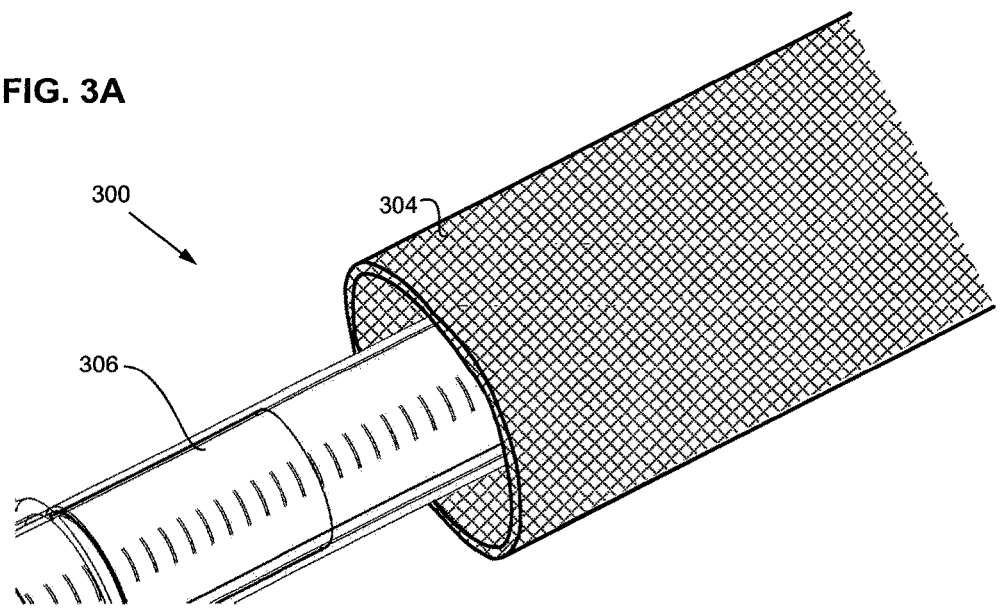
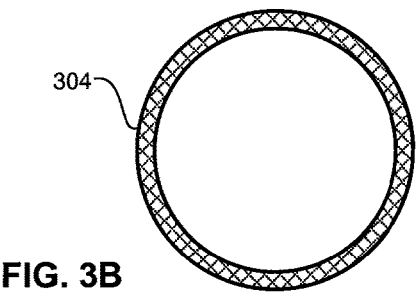
FIG. 3B

DELIVERY CATHETER SYSTEMS AND METHODS

This application is a continuation of U.S. patent application Ser. No. 16/846,158, filed on Apr. 10, 2020, which is a divisional application of U.S. patent application Ser. No. 14/508,556, filed Oct. 7, 2014, entitled "Delivery Catheter Systems and Methods," and these applications are incorporated herein by reference in their entirety to provide continuity of disclosure.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present disclosure relates to leadless cardiac pacemakers, and more particularly, to features and methods by which they are affixed within the heart. More specifically, the present disclosure relates to features and methods for delivering a leadless cardiac pacemaker to tissue.

BACKGROUND OF THE INVENTION

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the related applications cited above.

Self-contained or leadless pacemakers or other biostimulators are typically fixed to an intracardial implant site by an active engagement mechanism such as a screw or helical member that screws into the myocardium. Despite the numerous advantages provided by leadless pacemakers, there are challenges that need to be addressed with respect to the delivery systems and methods employed with leadless pacemakers.

BRIEF SUMMARY OF THE INVENTION

Disclosed herein is a delivery catheter for implanting a leadless biostimulator including a proximal region, a distal region and an exterior surface extending between the proximal and distal regions. In one embodiment, the delivery catheter includes a tubular body, an atraumatic end, and a shaft. The tubular body includes a proximal end, a distal end, and a lumen extending through the tubular body between the proximal and distal ends. The atraumatic end is coupled to, and distally extends from, the distal end. The atraumatic end includes at least one of a braided, woven or mesh construction that defines a volume that is coaxial with the lumen and distally terminates as a distal opening in the atraumatic end. The volume of the braided construction may be substantially cylindrical and defined by the interior cylindrical wall surface of the braided construction and extends generally the length of the braided construction. The shaft extends through the lumen. The shaft includes a proximal portion and a distal portion opposite the proximal portion. The shaft and the tubular body are longitudinally displaceable relative to each other. When the distal portion of the shaft is releasably coupled to the proximal region of the leadless biostimulator, at least one of distally displacing the tubular body relative to the shaft or proximally displacing the shaft relative to the tubular body causes the leadless biostimulator to be received in the volume of the braided construction via the distal opening and the atraumatic end to expand and encompass the leadless biostimulator. Conversely, at least one of proximally displacing the tubular body relative to the shaft or distally displacing the shaft relative to the tubular body causes the leadless biostimulator to exit the volume of the braided construction via the distal opening and the atraumatic end to self-bias into a reduced diameter.

Alternatively, in one embodiment, the atraumatic end has an internal diameter that is substantially the same size as the outer diameter of the leadless biostimulator when the atraumatic end is in a neutral state such that the leadless biostimulator can be received in and removed from the volume of the braided construction without causing any significant change to the diameter of the atraumatic end. The braided construction has sufficient shape memory characteristics to cause the atraumatic end to resume its neutral state when the atraumatic end is compressed into a reduced diameter in order to pass through an introducer.

The shaft may extend through the volume of the braided construction. In one embodiment, the atraumatic end being forced against the exterior surface of the biostimulator causes the atraumatic end to expand.

The atraumatic end may include a dual-wall construction. In one embodiment, the dual-wall construction is a result of a tubular braid, weave, or mesh rolled or folded back on itself, a resulting fold of the dual-wall construction defining a leading distal edge of the atraumatic end that defines the distal opening of the atraumatic end. The leading distal edge may have a bullnose longitudinal cross section. The leading distal edge may define at least a portion of a funnel configuration of the distal opening of the atraumatic end.

The dual-wall construction may support a liner or seal layer. The liner or seal layer may be located between an outer wall and an inner wall of the dual-wall construction.

The dual-wall construction may include an inner wall, an outer wall, and a wire reinforcement located between the inner and outer walls. The wire reinforcement may include at least one of longitudinally extending wires, radially extending wire rings, or a lattice of longitudinally extending wires and radially extending wire rings. The dual-wall construction may include an inner wall, an outer wall, and a reinforcing ring located between the inner and outer walls near the leading distal edge of the atraumatic end.

Also disclosed herein is another delivery catheter for implanting a leadless biostimulator including a proximal region, a distal region and an exterior surface extending between the proximal and distal regions. In one embodiment, the delivery catheter includes a tubular body, an atraumatic end, and a shaft. The tubular body includes a proximal end, a distal end, and a lumen extending through the tubular body between the proximal and distal ends. The atraumatic end is coupled to, and distally extends from, the distal end. The atraumatic end includes an expandable tubular portion including a longitudinally extending fold. The atraumatic end further includes at least one of a braided, woven or mesh construction that extends along a leading distal edge of the expandable tubular portion. The expandable tubular portion defines a volume that is coaxial with the lumen and distally terminates as a distal opening in the atraumatic end. The volume of the expandable tubular portion may be substantially cylindrical and defined by the interior cylindrical wall surface of the expandable tubular portion and extends generally the length of the expandable tubular portion. The fold and the at least one of a braided, woven or mesh construction are configured to facilitate the atraumatic end changing diameter. The shaft extends through the lumen. The shaft includes a proximal portion and a distal portion opposite the proximal portion. The shaft and the tubular body are longitudinally displaceable relative to each other. When the distal portion of the shaft is releasably coupled to the proximal region of the leadless biostimulator, at least one of distally displacing the tubular body relative to the shaft or proximally displacing the shaft relative to the tubular body causes the leadless biostimulator to be received in the volume of the expandable tubular portion via the distal opening and the atraumatic end to expand and encompass the leadless biostimulator. Conversely, at least one of proximally displacing the tubular body relative to the shaft or distally displacing the shaft relative to the tubular body causes the leadless biostimulator to exit the volume of the expandable tubular portion via the distal opening and the atraumatic end to self-bias into a reduced diameter.

Alternatively, in one embodiment, the expandable tubular body is actually a compressible tubular body with an internal diameter that is substantially the same size as the outer diameter of the leadless biostimulator when the atraumatic end is in a neutral state such that the leadless biostimulator can be received in and removed from the volume of the compressible tubular body without causing any significant change to the diameter of the atraumatic end.

The shaft may also extend through the volume of the compressible or expandable tubular body, as the case may be. In one embodiment, the atraumatic end being forced against the exterior surface of the biostimulator causes the atraumatic end to expand.

The at least one of a braided, woven or mesh construction may include a dual-wall construction. In one embodiment, the dual-wall construction is a result of a tubular braid, weave, or mesh rolled or folded back on itself. A resulting fold of the dual-wall construction defines a leading distal edge of the atraumatic end that defines the distal opening of the atraumatic end.

Also disclosed herein is a method of manufacturing a delivery catheter. In one embodiment, the method includes: manufacturing an atraumatic end of the delivery catheter by folding or rolling a cylindrical wall of a tube back on itself to form a dual-wall construction that defines at least a portion of the atraumatic end, the tube including at least one of a braided, woven or mesh construction; and securing the atraumatic end to a distal end of a polymer tubular body of the delivery catheter.

In one embodiment of the method, the dual-wall construction includes an inner wall, an outer wall, a cylindrical inner volume defined by the inner wall, a folded end defining a first circular opening of the inner volume, and free ends of the inner and outer walls, the free ends defining a second circular opening of the inner volume opposite the first circular opening.

The method may also include locating a sealing layer or stiffening structure between the inner and outer walls of the dual-wall construction. A ring structure may be located between the inner and outer walls of the dual-wall construction near the folded end. The ring may be segmented or discontinuous about its circumferential extent. Conversely, the ring may be non-segmented or continuous about its circumferential extent. The ring may be radiopaque and visible via fluoroscopy. The ring may be inflatable. The folded end may have a funnel configuration. A polymer may be reflowed about the free ends and then used to secure the atraumatic end to the tubular body of the delivery catheter.

BRIEF DESCRIPTION OF THE DRAWINGS

The novel features of the systems and methods disclosed herein are set forth with particularity in the claims that follow. A better understanding of the features and advantages of the systems and methods disclosed herein will be obtained by reference to the following detailed description that sets forth illustrative embodiments, in which the principles of the systems and methods are utilized, and the accompanying drawings of which:

FIGS. 3A-3B are schematic side and cross-sectional views of a pacemaker sheath.

DETAILED DESCRIPTION

Figure 1:
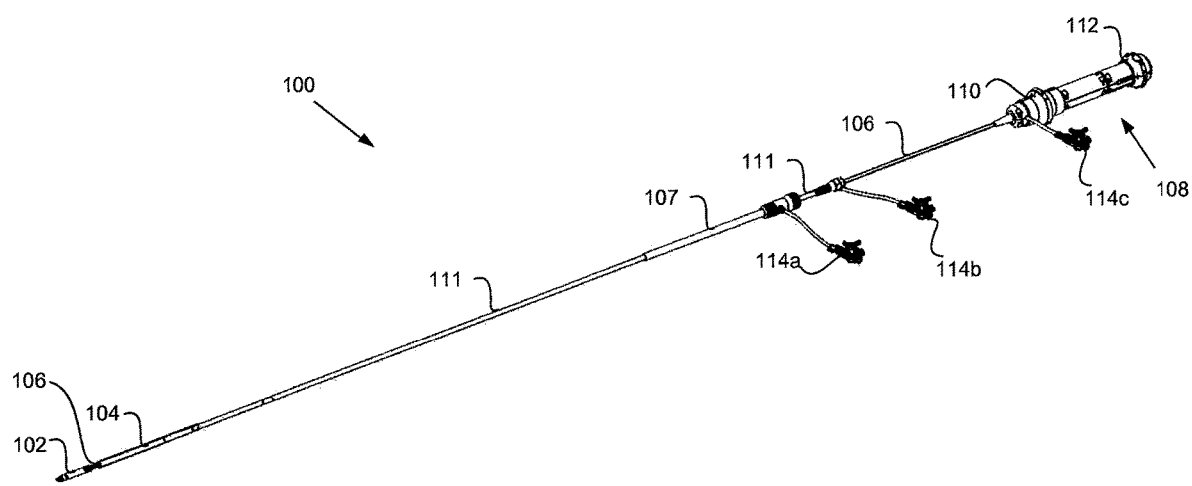
FIG. 1 is one embodiment of a delivery system for delivering a leadless pacemaker.

Various embodiments for delivering system comprising one or more leadless cardiac pacemakers or biostimulators are described. A leadless cardiac pacemaker can communicate by conducted communication, representing a substantial departure from conventional pacing systems. For example, an illustrative cardiac pacing system can perform cardiac pacing that has many of the advantages of conventional cardiac pacemakers while extending performance, functionality, and operating characteristics with one or more of several improvements.

In some embodiments of a cardiac pacing system, cardiac pacing is provided without a pulse generator located in the pectoral region or abdomen, without an electrode-lead separate from the pulse generator, without a communication coil or antenna, and without an additional requirement on battery power for transmitted communication.

An embodiment of a cardiac pacing system configured to attain these characteristics comprises a leadless cardiac pacemaker that is substantially enclosed in a hermetic housing suitable for placement on or attachment to the inside or outside of a cardiac chamber. The pacemaker can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for delivery and implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Self-contained or leadless pacemakers or other biostimulators are typically fixed to an intracardial implant site by an actively engaging mechanism or primary fixation mechanism such as a screw or helical member that screws into the myocardium. Examples of such leadless biostimulators are described in the following publications, the disclosures of which are incorporated by reference: (1) U.S. Pat. No. 8,457,742; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088397A1 on Apr. 19, 2007; (4) U.S. Pat. No. 8,352,025; (5) U.S. Pat. No. 7,937,148; (6) U.S. Pat. No. 7,945,333; (7) U.S. Pat. No. 8,010,209; and (8) International Application No. PCT/US2006/040564, filed on Oct. 13, 2006, entitled "Leadless Cardiac Pacemaker and System" and published as WO07047681A2 on Apr. 26, 2007.

In addition to the primary fixation mechanism, such as a helix, some biostimulators may further include a secondary fixation mechanism to provide another feature for keeping the biostimulator in place within the body. Secondary fixation mechanisms can be either active (e.g., the secondary fixation mechanism can actively engage tissue, either within or outside the heart), or can be passive (e.g., the secondary fixation mechanism is not attached to tissue but rather prevents the biostimulator from moving around in the body in the case of accidental detachment). Further details on secondary fixation mechanisms can be found in U.S. application Ser. No. 12/698,969.

Leadless pacemakers or biostimulators can be delivered to and retrieved from a patient using any of the delivery systems described herein. In some embodiments, a biostimulator is attached or connected to a delivery system and advanced intravenously into the heart. The delivery system can include features to engage the biostimulator to allow fixation of the biostimulator to tissue. For example, in embodiments where the biostimulator includes an active engaging mechanism, such as a screw or helical member, the delivery system can include a docking cap or key configured to engage the biostimulator and apply torque to screw the active engaging mechanism into the tissue. In other embodiments, the delivery system includes clips designed to match the shape of a feature on the biostimulator and apply torque to screw the active engaging mechanism into the tissue.

The delivery system can also include atraumatic tip configurations that can be extended over the leadless pacemaker and primary fixation mechanism when the leadless pacemaker is being delivered into, or withdrawn from, the patient. The atraumatic tip configurations can also be retracted from about the leadless pacemaker and primary fixation mechanism when the primary fixation mechanism is caused to displace relative to the heart tissue such as when the primary fixation mechanism in the form of a helix is screwed into or out of the heart tissue at an implantation site.

FIG. 1 illustrates a pacemaker delivery system 100 configured for delivery of a leadless pacemaker 102 into a patient. Delivery system 100 can include a guide catheter sheath 111 including an atraumatic distal end 104 in the form of a pacemaker sheath 104. Delivery system 100 can also have a pacemaker introducer sheath 107 and a catheter shaft 106. Catheter shaft 106 includes at its proximal end a handle 108, deflection knob 110, and tether shuttle 112. Each of longitudinal bodies 107, 111, 106 includes a flush port 114a, 114b, 114c extending respectively therefrom. As can be understood from FIG. 1, catheter shaft 106 extends through guide catheter sheath 111, which extends through introducer sheath 107. Each of longitudinal bodies 106, 107, 111 are displaceable proximal-distal relative to each other.

As discussed in greater detail below, atraumatic pacemaker sheath 104 may have a braided or woven construction that is sufficiently flexible to allow atraumatic pacemaker sheath 104 to encompass leadless pacemaker 102 or to have a diameter that is smaller than a diameter of leadless pacemaker 102 when not encompassing leadless pacemaker 102. The deflection knob 110 can be used to deflect catheter shaft 106 within catheter sheath 111 to steer and guide the catheter during implantation and/or removal of the pacemaker. Flush ports 114a, 114b, and 114c can be used to flush saline or other fluids through the catheter. Atraumatic sheath 104 forms the distal most region of catheter sheath 111. Catheter sheath 111 can be advanced distally over catheter shaft 106 such that atraumatic sheath 104 is caused to extend over leadless pacemaker 102. Also, the distal displacement of catheter sheath 111 relative to catheter shaft 106 can be used to provide additional steering and support for the delivery catheter during implantation and to surround the pacemaker as it is introduced through a trocar or introducer sheath 107 into the patient. Catheter sheath 111 can be retracted proximally over catheter shaft 106 such that atraumatic sheath 104 is caused to retract from over leadless pacemaker 102, the braided construction of atraumatic sheath 104 being such that atraumatic sheath 104 self-biases into a reduced diameter. In one embodiment, the reduced diameter of atraumatic sheath 104 will be no greater than the diameter of leadless pacemaker 102.

Figure 2A:
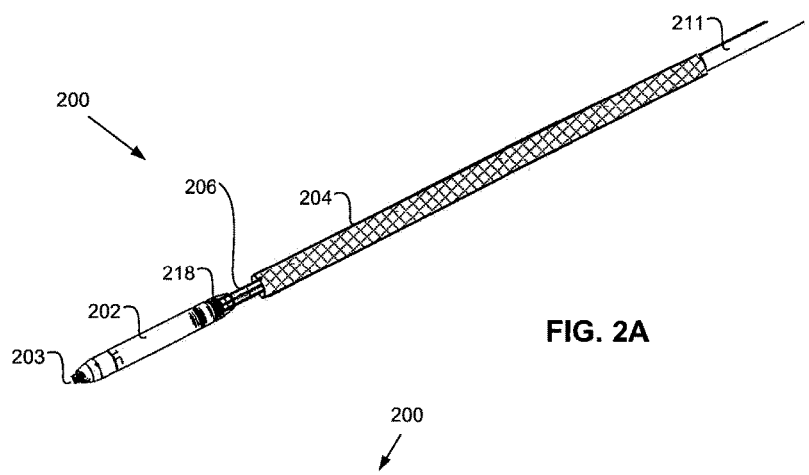
FIG. 2A is a close-up view of a distal portion of the delivery system with an atraumatic end of the delivery system proximal of the leadless pacemaker.
Figure 2B:
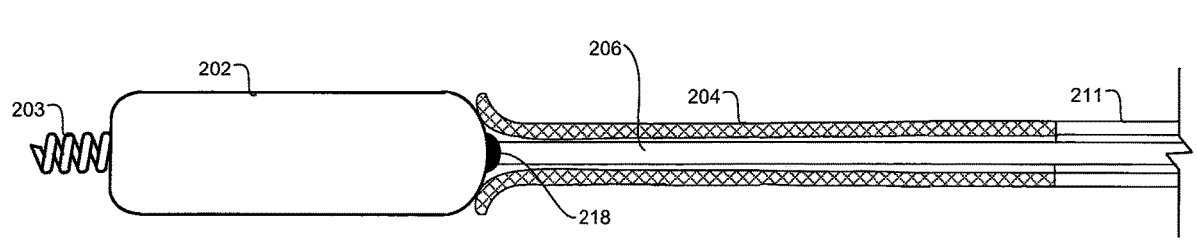
FIG. 2B is a diagrammatic longitudinal cross section of the leadless pacemaker and delivery system in the condition illustrated in FIG. 2A.

Alternatively, pacemaker sheath 104 may have a neutral shape it assumes or biases into wherein its internal diameter is the same as the outer diameter of leadless pacemaker 102 such that the pacemaker sheath can readily slip over and off of the leadless pacemaker without the pacemaker sheath changing its internal diameter. However, on account of the flexibility and shape memory nature of the pacemaker sheath, the pacemaker sheath can be compressed for passage through introducer 107 and, once through the introducer, the shape memory nature of the pacemaker sheath causes the pacemaker sheath to assume its neutral shape with its internal diameter that is the same as the outer diameter of the leadless pacemaker. FIG. 2A is a close-up view of a distal portion of delivery system 200 and pacemaker 202, and FIG. 2B is a diagrammatic longitudinal cross section of the same components in the same condition. The pacemaker 202 of FIGS. 2A and 2B can include a helix 203 for attachment of the pacemaker to tissue. In FIGS. 2A and 2B, the pacemaker is attached to docking cap 218 of catheter shaft 206. Atraumatic pacemaker sheath 204, along with the rest of guide catheter sheath 211, is shown pulled back proximally along catheter shaft 206 to expose pacemaker 202 and helix 203. Thus, when guide catheter sheath 211 is pulled back proximally thereby causing its atraumatic distal end region 204 to pull back proximally, as shown in FIGS. 2A and 2B, pacemaker 202 is in an exposed, delivery configuration such that helix 203 is exposed for screwing into or out of heart tissue at a implantation target site.

Figure 2C:
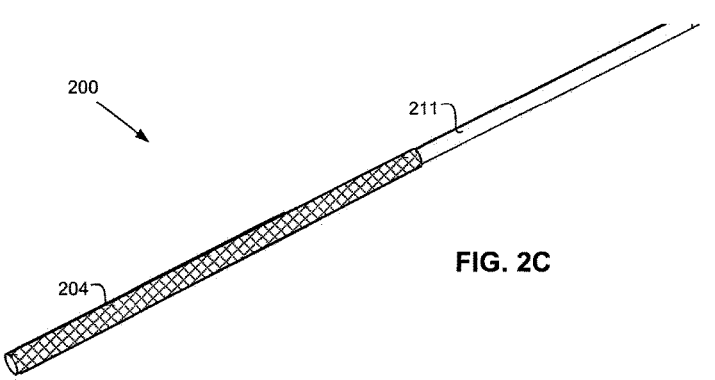
FIG. 2C is the same view as FIG. 2A, except the atraumatic end of the delivery system has been distally displaced over the leadless pacemaker.
Figure 2D:
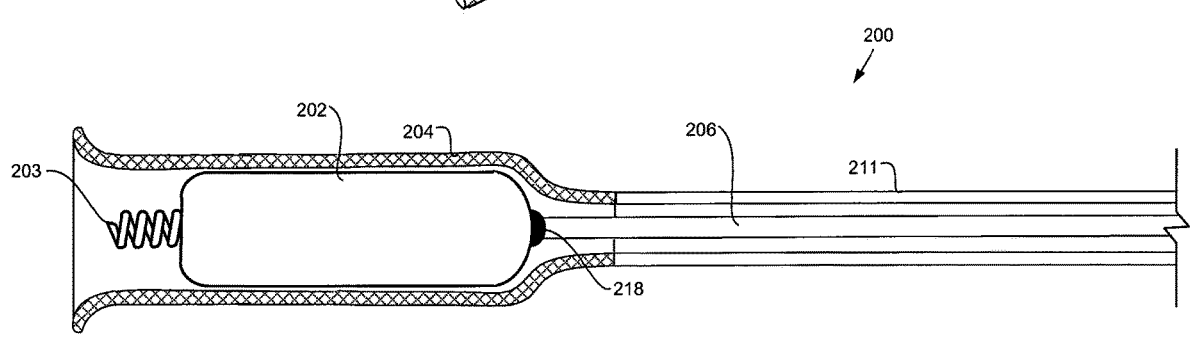
FIG. 2D is a diagrammatic longitudinal cross section of the leadless pacemaker and delivery system in the condition illustrated in FIG. 2C.

In FIGS. 2C and 2D, guide catheter sheath 211 is extended distally to cause atraumatic pacemaker sheath 204 to cover catheter shaft 206, pacemaker 202, and helix 203 to protect patient tissue from the sharp edges of helix 203 during implantation. Thus, when catheter sheath 211 and its atraumatic distal end region 204 in the form of pacemaker sheath 204 are advanced distally to protect the pacemaker and helix, as shown in FIGS. 2C and 2D, the pacemaker 202 and helix 203 are in a protected, advancement configuration.

FIG. 3A is a close-up view of atraumatic distal end region 204 or pacemaker sheath 304 of catheter sheath 311 (shown in FIG. 3K) of delivery system 300. FIG. 3B is a transverse cross section of only pacemaker sheath 304. As shown, pacemaker sheath 304 includes a braided, woven or mesh construction, which is configured to minimize the potential for the helix to become stuck in the braided, woven or mesh construction. For example, in one embodiment to minimize the likelihood of a helix of a common size and configuration becoming stuck in the braided construction, the braided construction includes 72-144 #wires with a diameter of between approximately 0.0015 inch and approximately 0.006 inch. Other braided constructions may be employed to minimize the helix becoming stuck in the braided construction where the helix is of an uncommon size or configuration.

The wires of the braided construction may be made of metal materials such as, for example, nickel-titanium alloy ("Nitinol"), cobalt-chromium-nickel alloy ("Elgioly"), 316 stainless steel, 304 stainless steel, or etc. In one embodiment, some of the wires (e.g., one, two, three, four, or more wires) or all of the wires of the braided construction may be of a radiopaque material such as tungsten, platinum, gold, or etc. to facilitate the braided construction being visible via fluoroscopy. In some embodiments, the wires may have a diameter range of approximately 0.001 inch to approximately 0.005 inch, and the length of pacemaker sheath 304 may have a range of approximately 1 cm to approximately 10 cm with a preferred length range of approximately 5 cm to approximately 7 cm, depending on the length of the leadless pacemaker to be received in the pacemaker sheath. In one embodiment, the braided construction may be woven from polymer materials such as, for example, polyether block amide ("PEBAX"), polyethylene terephthalate ("PET"), polyethylene ("PE"), nylon, urethane, polyester, or a blend of any of the aforementioned where appropriate.

Figure 3C:
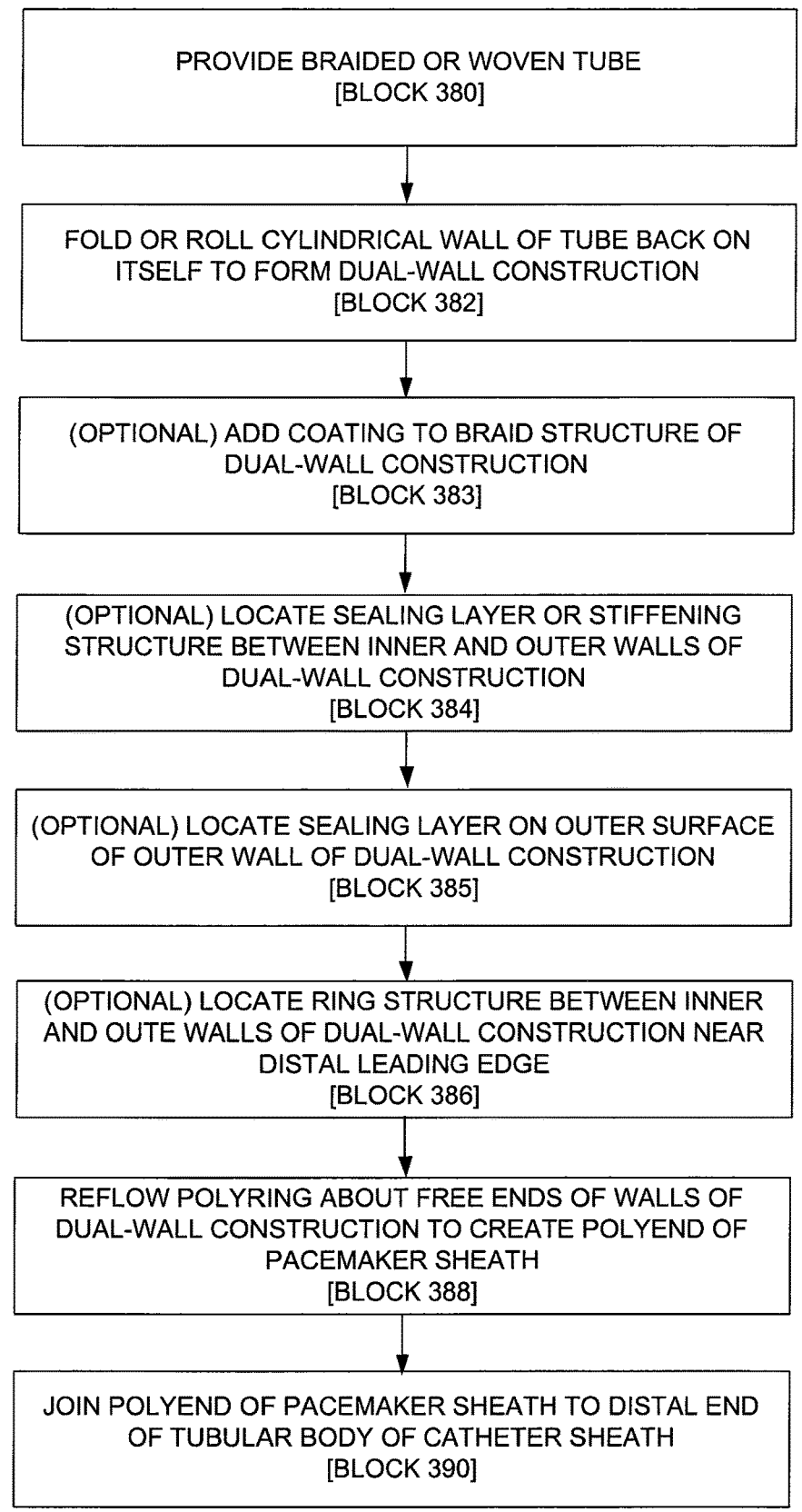
FIG. 3C is a flow chart outlining a method of manufacturing the pacemaker sheath and its joining to a tubular body of the catheter sheath to become part of the catheter sheath.
Figure 3D:
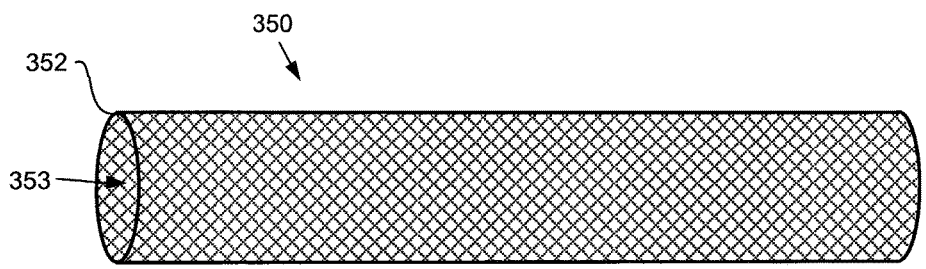
FIG. 3D is an isometric view of a braided or woven tube used in the manufacture of the pacemaker sheath as outlined in FIG. 3C.

In one embodiment, the pacemaker sheath 304 is manufactured and coupled to the rest of the catheter sheath 311 via the following methodology, which is outlined in the flow chart of FIG. 3C. FIG. 3D is an isometric view of a cylindrical braided tube 350 used to manufacture the pacemaker sheath, and this tube 350 is provided as part of the manufacturing process [block 380 of FIG. 3C]. The braided tube 350 has a cylindrical wall 352 with a woven or braided construction formed of the above-mentioned wires and materials, the cylindrical wall defining a cylindrical interior 353.

Figure 3E:
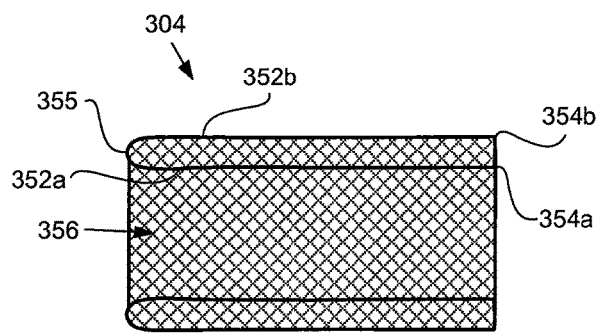
FIGS. 3E-3F are longitudinal cross sections of the tube of FIG. 3D folded or rolled back on itself to form a dual-wall construction that becomes the pacemaker sheath, as outlined in FIG. 3C.

FIG. 3E is a longitudinal cross section of cylindrical wall 352 after it has been folded or rolled back on itself to form a dual-wall construction having an inner wall 352a and an outer wall 352b [block 382 of FIG. 3C]. Each wall 352a, 352b has a respective free end 354a, 354b, and the distal or leading edge 355 of the resulting pacemaker sheath 304 is a bullnose or rounded edge 355 resulting from the folding of cylindrical wall 352 back on itself. Another cylindrical interior space 356 is defined by the dual-wall construction.

Figure 3F:
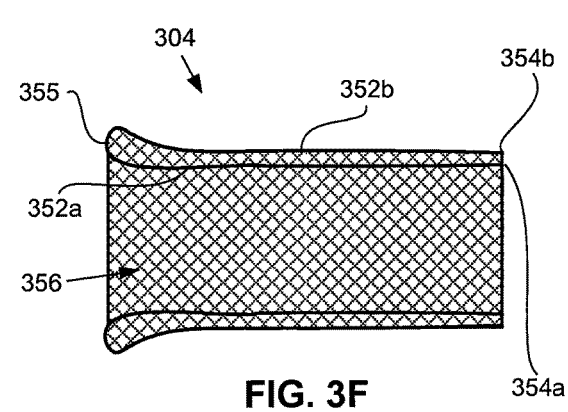

As illustrated in FIG. 3F, which is the same view as FIG. 3E, except with a different result, in some embodiments, distal leading edge 355 of pacemaker sheath 304 is flared or funnel shaped to facilitate the pacemaker sheath extending over the leadless pacemaker, as can be understood from FIGS. 2A-2B. This flared or funnel shaped edge 355 illustrated in FIG. 3F can be heat set to maintain the funnel shape. In one embodiment, the pacemaker sheath or at least the flared or funnel shaped edge can be dip coated to mitigate any threaded protrusions of the braid, thereby reducing the chance of interferences resulting from such protrusions.

In one optional embodiment, the pacemaker sheath 304 can be coated with a hydrophilic, drug or parylene coating to inhibit or prevent thrombus [block 383 of FIG. 3C]. Such coatings are advantageous if the pacemaker sheath does not include a liner layer on the outside of the pacemaker sheath as described below with respect to block 385 of FIG. 3C.

Figure 3G:
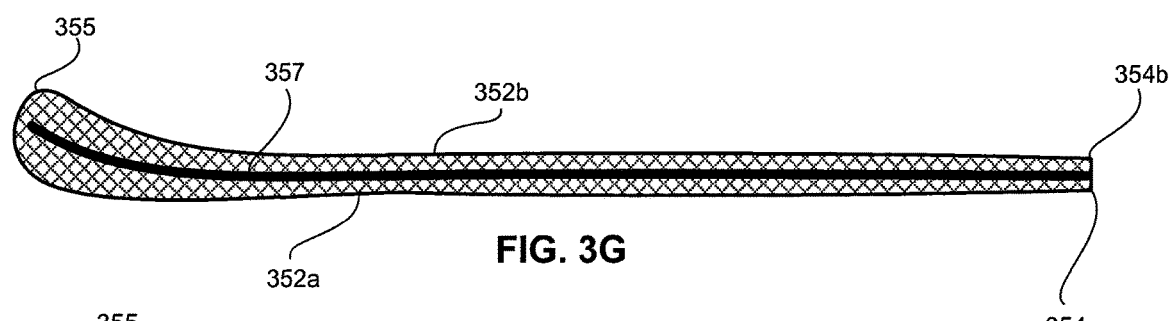
FIGS. 3G-3H are each an enlarged longitudinal cross section of one of the dual-wall constructions of the pacemaker sheath of FIG. 3E or 3F showing optional structures located within the dual-wall construction.

FIG. 3G is an enlarged longitudinal cross section of one of the dual-wall arrangements of pacemaker sheath 304 of FIG. 3E or 3F. As shown in FIG. 3G, in one optional embodiment, a structure or layer 357 extends through the dual-wall construction between inner and outer walls 352a, 352b [block 384 of FIG. 3C]. In one embodiment, the layer 357 is a liner or sealing layer formed of a polymer material such as polyurethane, PEBAX, nylon, polyester, polyurethane, PTFE, EPTFE, or appropriate blends of these materials such as a polyester-polyurethane blend. The layer 357 may have a durometer of approximately 25 to approximately 72 on scale D. The layer 357 may have a thickness of between approximately 0.0001 inch and approximately 0.005 inch. In one embodiment, liner layer 357 is 0.001 inch thick polyurethane.

In one embodiment that is not explicitly shown in the figures, instead of liner layer 357 being located between walls 352a, 352b, liner layer 357 is supported on the dual-wall construction so as to extend along the inner circumferential surface of inner wall 352a such that the liner layer defines cylindrical inner volume 356.

In one embodiment the structure 357 is a stiffening structure. In one embodiment stiffening structure 357 is a plurality of stiffening wires formed of the same type and size of wire forming the braided construction of sheath 304 as described above. In one embodiment, the stiffening wires may have a diameter range of approximately 0.003 inch and approximately 0.01 inch. The stiffening wires may be in the form of a plurality of longitudinally extending wires evenly radially dispersed in the space between the inner and outer walls. Alternatively, the stiffening wires may be in the form of a plurality of radial rings evenly longitudinally dispersed in the space between the inner and outer walls. In yet another alternative, the plurality of longitudinally extending wires and plurality of radial rings may be combined to form a wire mesh or lattice between the inner and outer walls. Regardless of how the stiffening wires are arranged between the inner and outer walls, the stiffening wires increase the column strength of the pacemaker sheath.

Figure 3H:
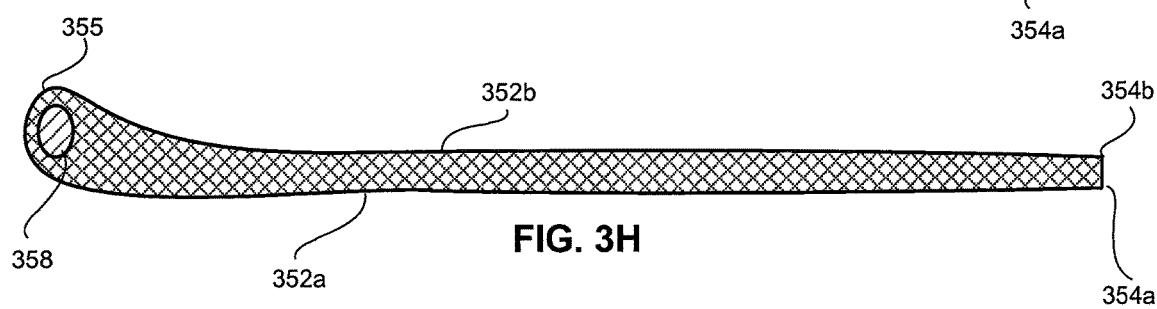
Figure 3I:
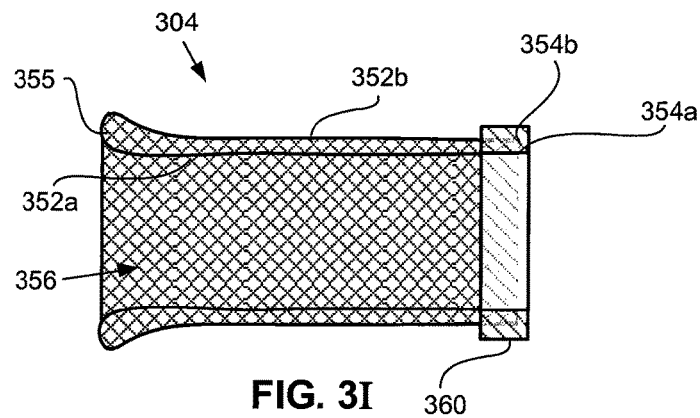
FIG. 3I-3K are the same views as FIGS. 3E-3F, except further along in the manufacturing process outlined in FIG. 3C.
Figure 3J:
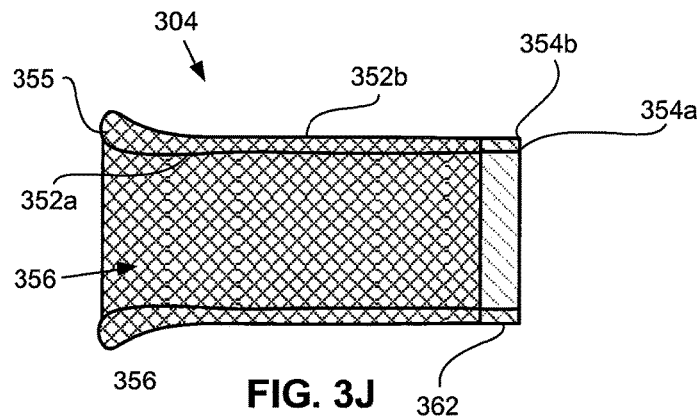
Figure 3K:
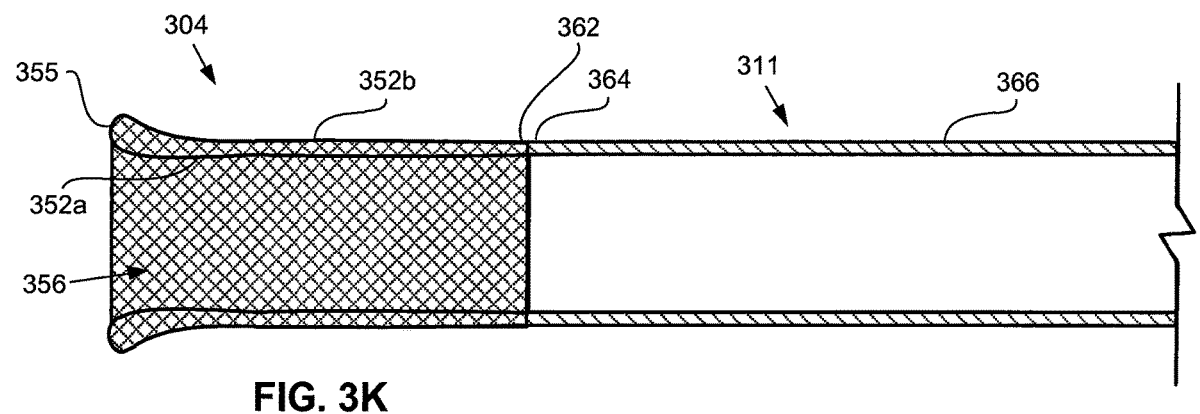
Figure 3L:
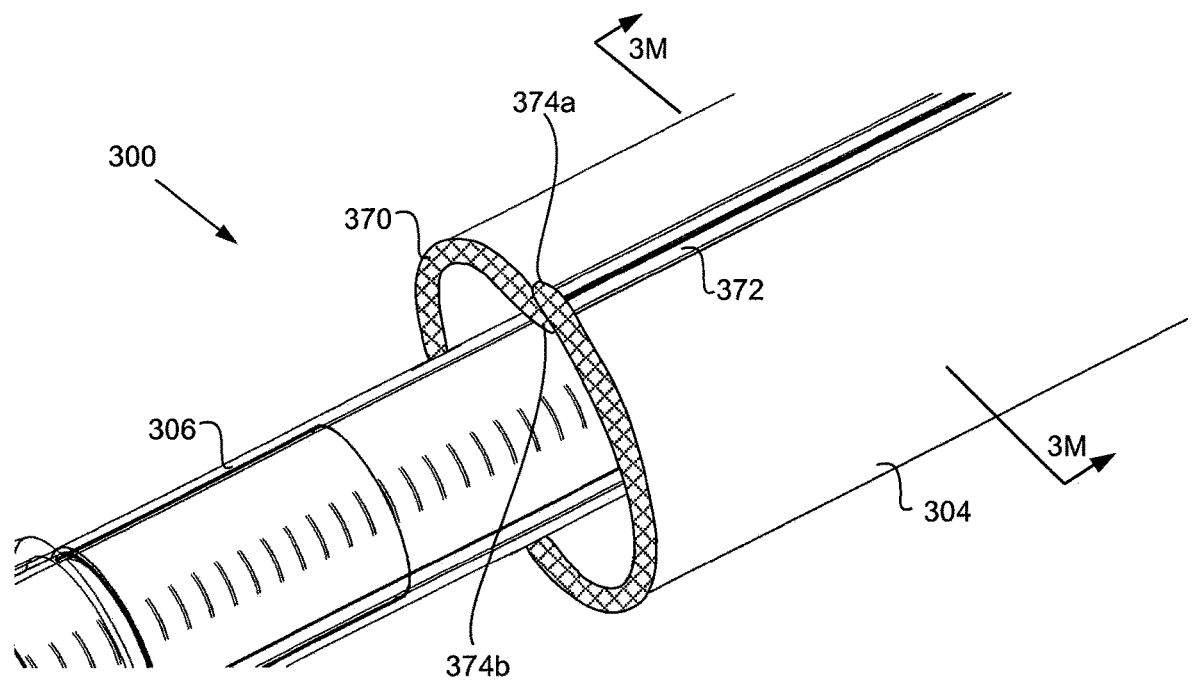
FIG. 3L is the same view as FIG. 3A, except of another embodiment.
Figure 3M:
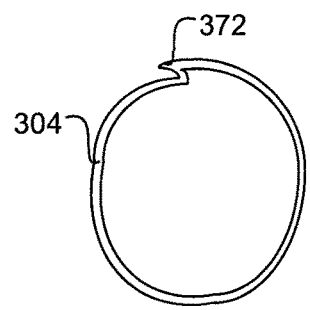
FIG. 3M is a transverse cross section of the pacemaker lead as taken along section line 3M-3M of FIG. 3L.
Figure 3N:
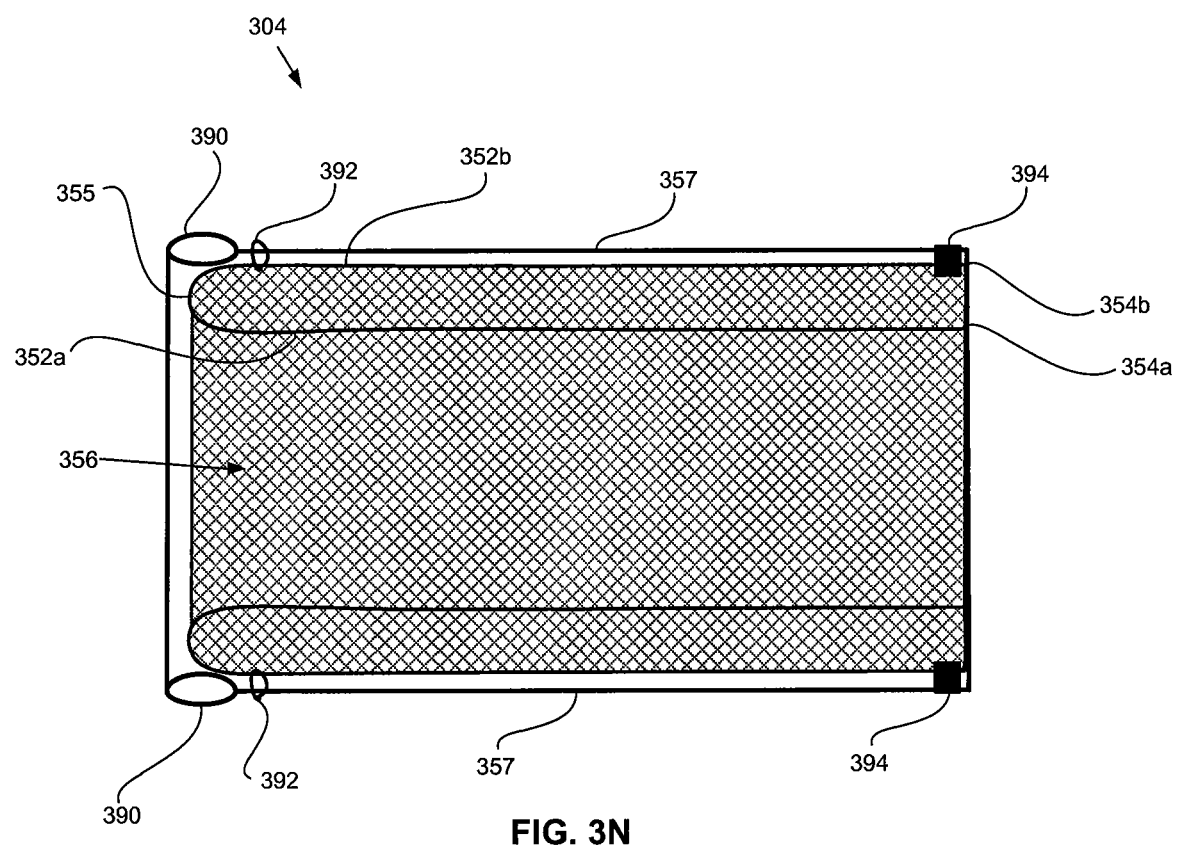
FIG. 3N is a longitudinal cross section of an embodiment where the liner layer is on the exterior of the braided construction.
Figure 3O:
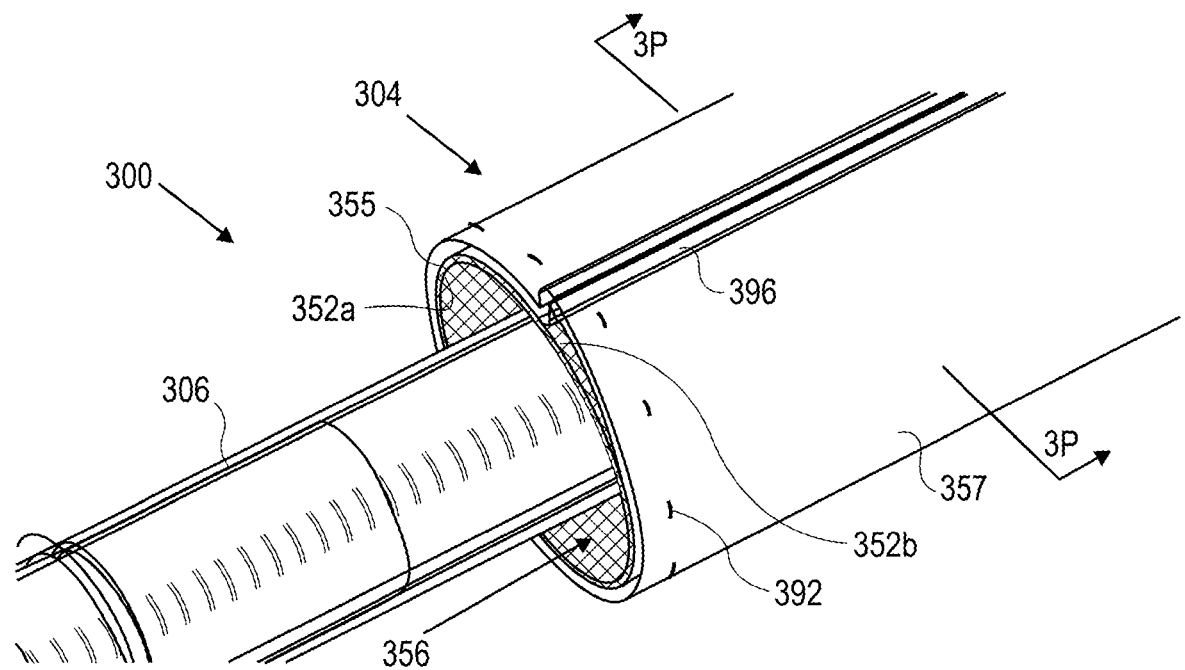
FIG. 3O is an isometric view of the pacemaker sheath of FIG. 3N.
Figure 3P:
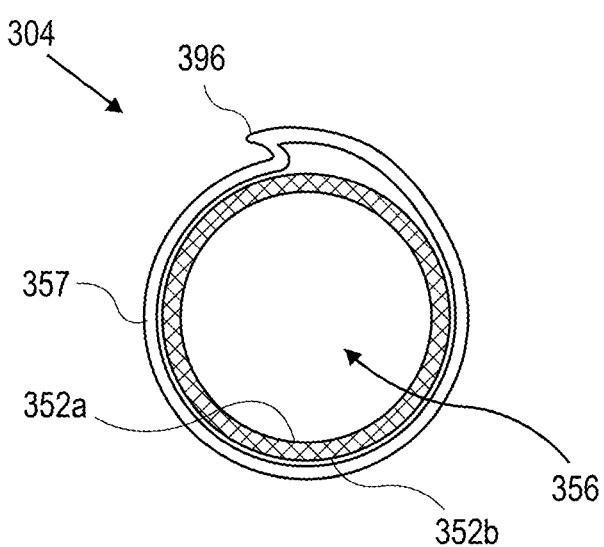
FIG. 3P is a transverse cross section of the pacemaker sheath as taken along section line P-P in FIG. 3O.

In one optional embodiment as illustrated in FIG. 3N-3P, instead of liner layer 357 being located between walls 352a, 352b, liner layer 357 is supported on the dual-wall construction so as to extend along the outer circumferential surface of outer wall 352b such that the liner layer defines the cylindrical outer circumference of pacemaker sheath 304 [block 385 of FIG. 3C]. As illustrated in FIG. 3N, the distal end 390 of liner layer 357 may be rounded or folded back on itself to be atraumatic in configuration and may be generally flush with distal end 355 of the braided construction or may distally overhang distal end 355 by approximately 0.0 inch to approximately 0.2 inch. As shown in FIGS. 3N and 3O, the distal region of liner layer 357 may be secured to the braided construction via sutures 392. As illustrated in FIG. 3N, the proximal region of the liner layer may be secured to the braided construction via heat bonded regions 394. In some instances, some or all of the sutures 392 may be of a radiopaque material such as platinum-iridium alloy, platinum, gold or etc. to facilitate the visualization of the distal end of the pacemaker sheath under fluoroscopy. The liner layer 357 can distally terminate with edges that project distally generally straight or in an outwardly flared or funnel shape.

In some embodiments, liner layer 357 may be supported loosely or unrestrained on the underlying braided construction. In some embodiments, liner layer 357 may be laminated onto the underlying braided construction.

As indicated in FIGS. 3O and 3P, liner layer 357 may have a slit, seam, or fold 396 that allows the liner layer to expand and contract with the underlying braided construction as the pacemaker sleeve 304 moves across the exterior of the leadless pacemaker. By designing pacemaker sheath 304 with a slit, seam, or fold 396 in the liner layer that runs longitudinally along the sheath, the cross sectional diameter of the pacemaker sheath can be reduced by folding or overlapping the liner layer of the pacemaker sheath over itself at eh slit, seam or fold. Conversely, the cross sectional diameter of the pacemaker sheath can be increased by unfolding or expanding the slit, seam or fold.

FIG. 3H is also an enlarged longitudinal cross section of one of the dual-wall arrangements of pacemaker sheath 304 of FIG. 3E or 3F. As shown in FIG. 3H, in one optional embodiment, a ring structure 358 radially extends through the dual-wall construction between inner and outer walls 352a, 352b near distal leading edge 355 [block 386 of FIG. 3C]. In one embodiment, the ring structure 358 is formed of a radiopaque material such as platinum, platinum-iridium alloy, gold, barium filled polymer, tungsten, or etc. to be visible via fluoroscopy. The ring may have a thickness of between approximately 0.0005 inch and approximately 0.01 inch. Where the ring is barium filled polymer, the ring can be heat bonded to the liner layer 357 where present.

The ring may be segmented or discontinuous about its circumferential extent. Conversely, the ring may be non-segmented or continuous about its circumferential extent. In one embodiment, the ring structure 358 may be used to increase the radial strength or rigidity of the distal leading edge. In one embodiment, all the optional elements discussed with respect to FIGS. 3G and 3H are present in the pacemaker sheath.

FIGS. 3I, 3J and 3K are the same views as FIGS. 3E and 3F, except further along in the manufacturing process outlined in FIG. 3C. As shown in FIG. 3I, a polyring 360 is reflowed about the free ends 354a, 354b of walls 352a, 352b of pacemaker sheath 304 [block 388 of FIG. 3C] such that the polyring becomes a polyend 362 of the pacemaker sheath, as can be understood from FIG. 3J. The polyend of pacemaker sheath 304 is then mated with and reflowed onto, or otherwise connected with, a distal end 364 of a tubular body 366 of catheter sheath 311 [block 390 of FIG. 3C], as indicated in FIG. 3K. The resulting catheter sheath may then be assembled with the rest of its components and then combined as complete a catheter sheath 111 with introducer sheath 107 and catheter shaft 106 to become delivery system 100, as illustrated in FIG. 1.

In an alternative embodiment, instead of employing a braided pacemaker sheath as described above with respect to FIGS. 3A-3K, the pacemaker sheath only employs a braided atraumatic buffer portion 370 along its extreme distal edge. For example, as shown in FIGS. 3L and 3M, which are respectively the same views depicted in FIGS. 3A and 3B, pacemaker sheath 304 can include a crease or fold 372 along the length of the pacemaker sheath, and atraumatic braided portion or donut 370 extends along the extreme distal edge of pacemaker sheath 304 to provide an atraumatic buffer 370 on the leading extreme distal edge of the pacemaker sheath. The braided donut 370 may be manufactured from the aforementioned materials and via methods similar to those described above with respect to the embodiment of FIGS. 3A-3K.

By designing pacemaker sheath 304 with a fold 372 that runs longitudinally along the sheath, the cross sectional diameter of the pacemaker sheath can be reduced by folding the pacemaker sheath over itself. Thus, similar to already described above, during initial implantation of the pacemaker through a introducer sheath into the patient, the pacemaker sheath can be positioned just proximal to the pacemaker, and folded along fold 372 so as to have a cross sectional diameter close to or equal to the same diameter as the pacemaker. This allows a smaller diameter introducer sheath to be used than would normally be necessary, since those delivery systems must incorporate a larger introducer sheath to allow passage of a full sized pacemaker sheath. After the delivery system is inserted through the introducer sheath into the patient, the sheath can be advanced distally over the leadless pacemaker. Advancing the pacemaker sheath distally over the pacemaker causes fold 372 to unfold, thereby increasing the diameter of the pacemaker sheath so that it can slide over and cover the pacemaker and fixation helix. FIG. 3M is a cross sectional view of the pacemaker sheath 304 and fold 372 as taken along section line 3M-3M of FIG. 3L, giving another view on how the cross sectional diameter of the pacemaker sheath can increase and decrease. Since atraumatic donut 370 extends along the leading distal edge of the pacemaker sheath and the pacemaker sheath is radially discontinuous on account of its longitudinal fold 372, atraumatic donut 370 is also radially discontinuous such that its free ends 374a, 374b overlap each other as can be understood from FIG. 3L and in much the same way as the rest of the pacemaker sheath as depicted in FIGS. 3L and 3M.

During initial insertion of the delivery system into a patient, a physician can gain access to the patient's venous system with an introducer sheath using the Seldinger technique (not shown). The delivery system, including the leadless pacemaker, catheter sheath and catheter shaft, can then be advanced through the introducer sheath into the patient's venous system to facilitate delivery of the pacemaker into the heart. Reducing the diameter of the pacemaker, the delivery system, and thus the introducer sheath, provides for easier and less intrusive access to a patient's venous system.

As can be understood from FIGS. 2A-3K, pacemaker sheath 304 has a woven expandable configuration that self-biases to a reduced diameter that is at least as small as the diameter of the leadless pacemaker and is sufficiently readily expandable by simply distally displacing pacemaker sheath 304 against the leadless pacemaker such that sheath 304 expands about and envelopes leadless pacemaker. Thus, during initial implantation of the pacemaker through an introducer sheath into the patient, the pacemaker sheath can be positioned just proximal to the pacemaker, as illustrated in FIGS. 2A-2B, the diameter of the pacemaker sheath self-biasing to its minimum diameter so as to have a cross sectional diameter close to or equal to the same diameter as the pacemaker. This allows a smaller diameter introducer sheath to be used than would normally be necessary, since those delivery systems must incorporate a larger introducer sheath to allow passage of a full sized pacemaker sheath. After the delivery system is inserted through the introducer sheath into the patient, the sheath can be advanced distally over the leadless pacemaker. Advancing the pacemaker sheath distally over the pacemaker causes the braided or woven expandable configuration of the pacemaker sheath to expand sufficiently with respect to its diameter that the pacemaker sheath can slide over and cover the pacemaker and fixation helix, as illustrated in FIGS. 2C-2D, thereby preventing the helix from contacting patient tissue.

It should be noted that while the pacemaker sheath is shown in FIGS. 2B and 2D as having a neutral configuration with an internal diameter that is less than the outer diameter of the leadless pacemaker, thereby requiring the pacemaker sheath to expand as it is distally displaced over the leadless pacemaker for the leadless pacemaker to be received in the internal volume of the pacemaker sheath, in other embodiments, the pacemaker sheath has a neutral configuration with an internal diameter that is the same as the outer diameter of the leadless pacemaker. More specifically, pacemaker sheath 104 may have a neutral shape it assumes or biases into wherein its internal diameter is the same as the outer diameter of leadless pacemaker 102 such that the pacemaker sheath can readily slip over and off of the leadless pacemaker without the pacemaker sheath changing its internal diameter. However, on account of the flexibility and shape memory nature of the pacemaker sheath, the pacemaker sheath can be compressed for passage through introducer 107 and, once through the introducer, the shape memory nature of the pacemaker sheath causes the pacemaker sheath to assume its neutral shape with its internal diameter that is the same as the outer diameter of the leadless pacemaker.

Figure 4A:
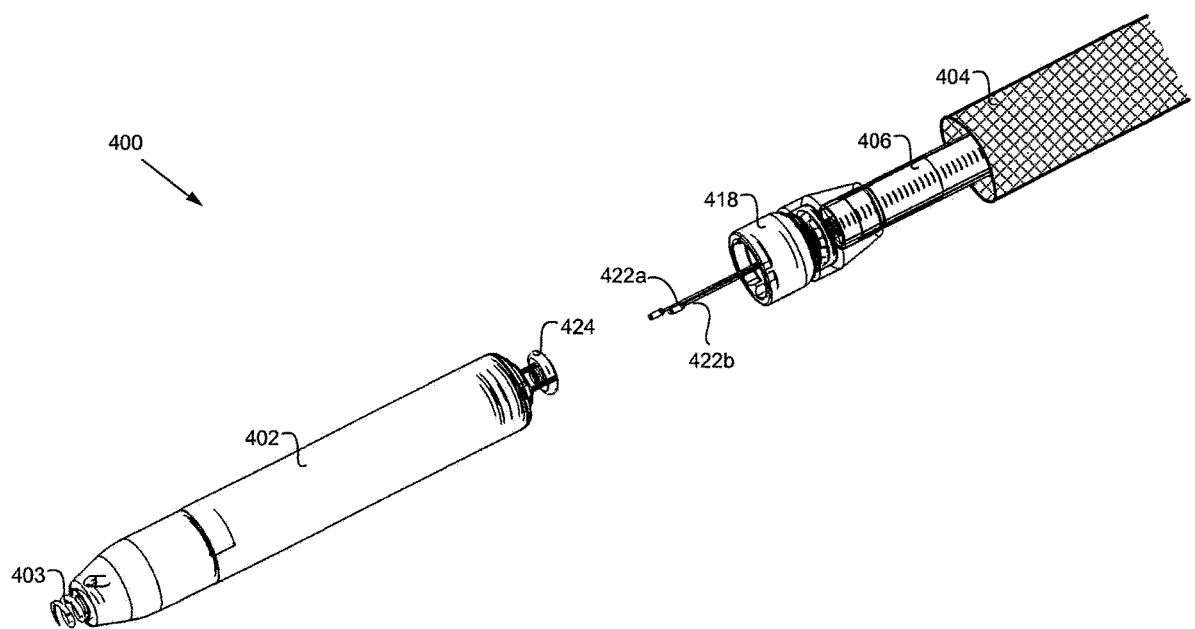
FIGS. 4A-4G are side views of a delivery system attached to a pacemaker.

FIG. 4A illustrates delivery system 400, including pacemaker 402 comprising helix 403 and attachment feature 424, and the delivery catheter comprising the distal region or pacemaker sheath 404 of the catheter sheath, catheter shaft 406, docking cap 418, and tethers 422a and 422b. The tethers can comprise wires, shafts, tubes, cords, ropes, strings, or other similar structures that can extend throughout the catheter shaft. In some embodiments, the tethers comprise a shape memory material, such as nitinol. In other embodiments, the tethers comprise stainless steel wires or braids. In FIG. 4A, the pacemaker 402 is not attached to docking cap 418 of the delivery catheter. The process of connecting the pacemaker to the delivery catheter will now be described.

Figure 4B:
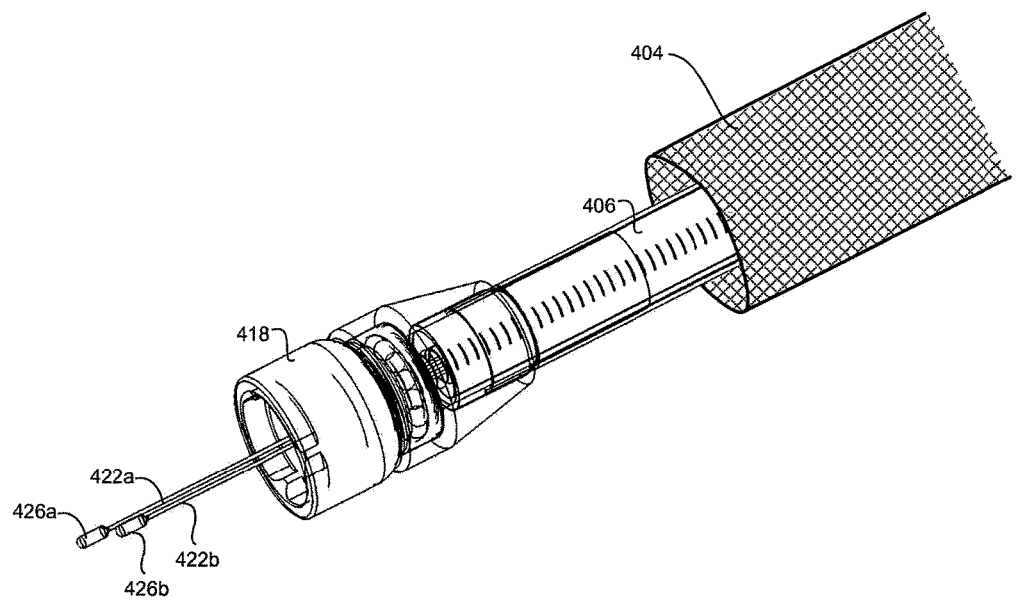

Referring to FIG. 4B, tethers 422a and 422b can include distal features 426a and 426b. The distal features can be, for example, features on the tethers that protrude radially from the tether, such as bumps, spheres, cylinders, rectangles, or other similar shapes extending outwards from the tethers. In some embodiments, the distal features can be expandable, such as balloons or expandable mechanical structures. Generally, the distal features have a cross sectional diameter larger than the cross sectional diameter of the tethers. As shown, in one embodiment, distal feature 422a can be advanced further from the catheter than distal feature 422b, so that when the tethers are pushed together, distal feature 422b rests against tether 422a. This causes the combined cross sectional diameter of both distal features and tethers to be less than if the distal features were lined up side by side. By way of comparison, in FIG. 4C the distal features 426a and 426b are lined up side by side and therefore have a greater combined cross sectional diameter when pressed together than is shown in FIG. 4B.

Figure 4C:
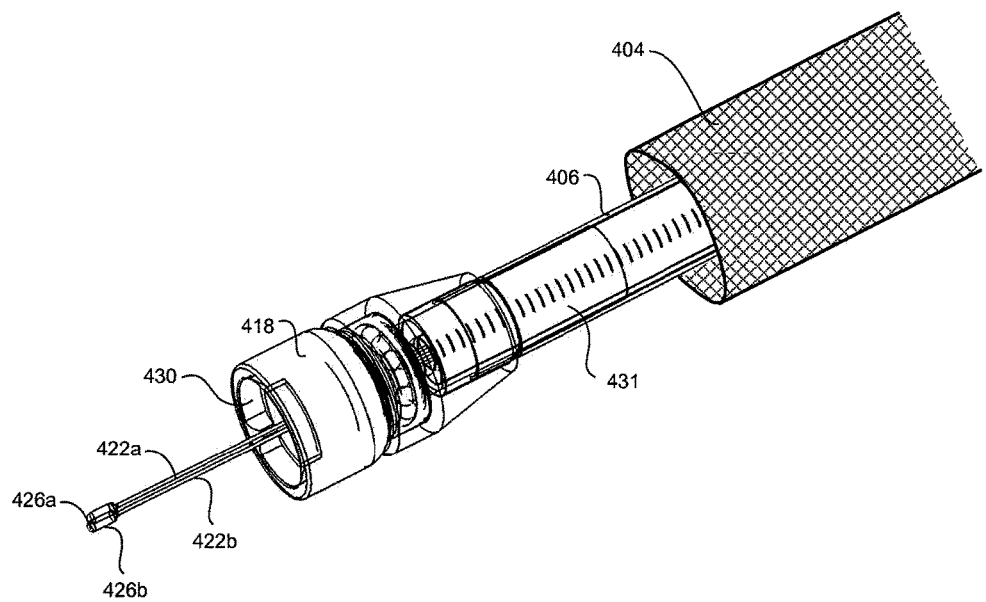
Figure 4D:
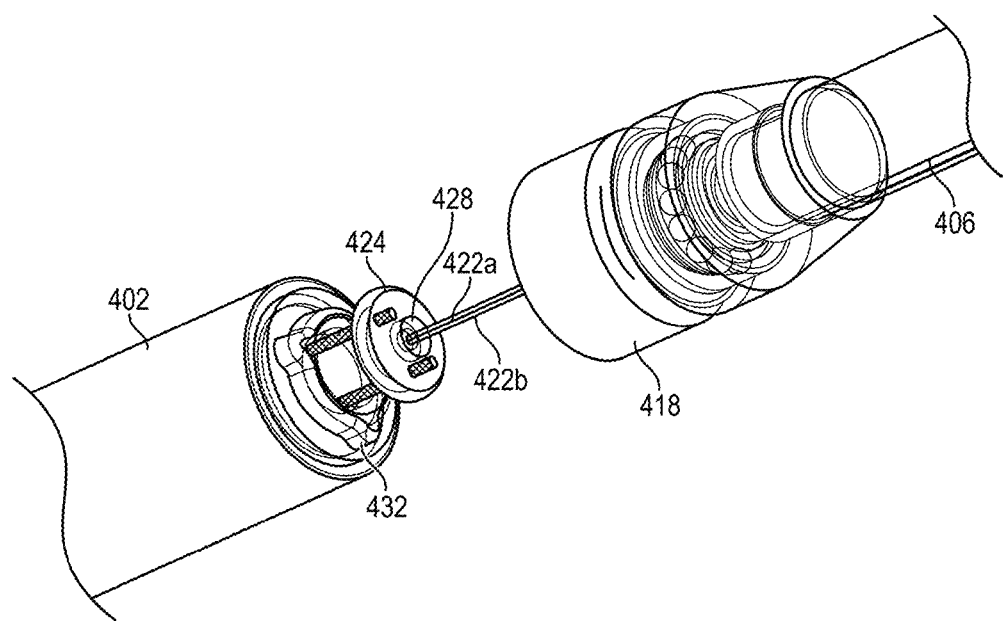
Figure 4E:
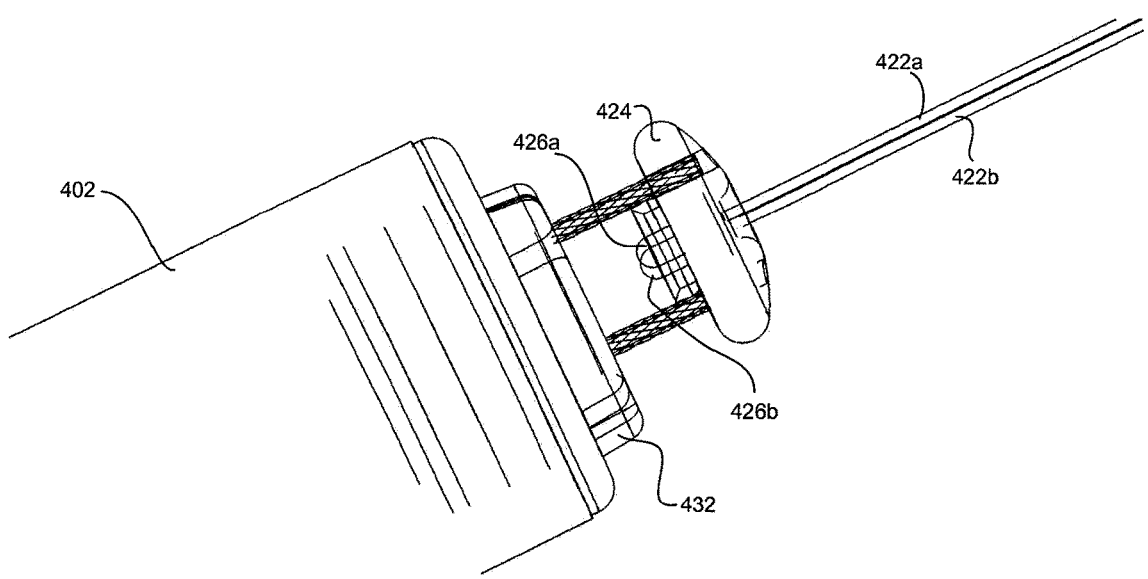
Figure 4F:
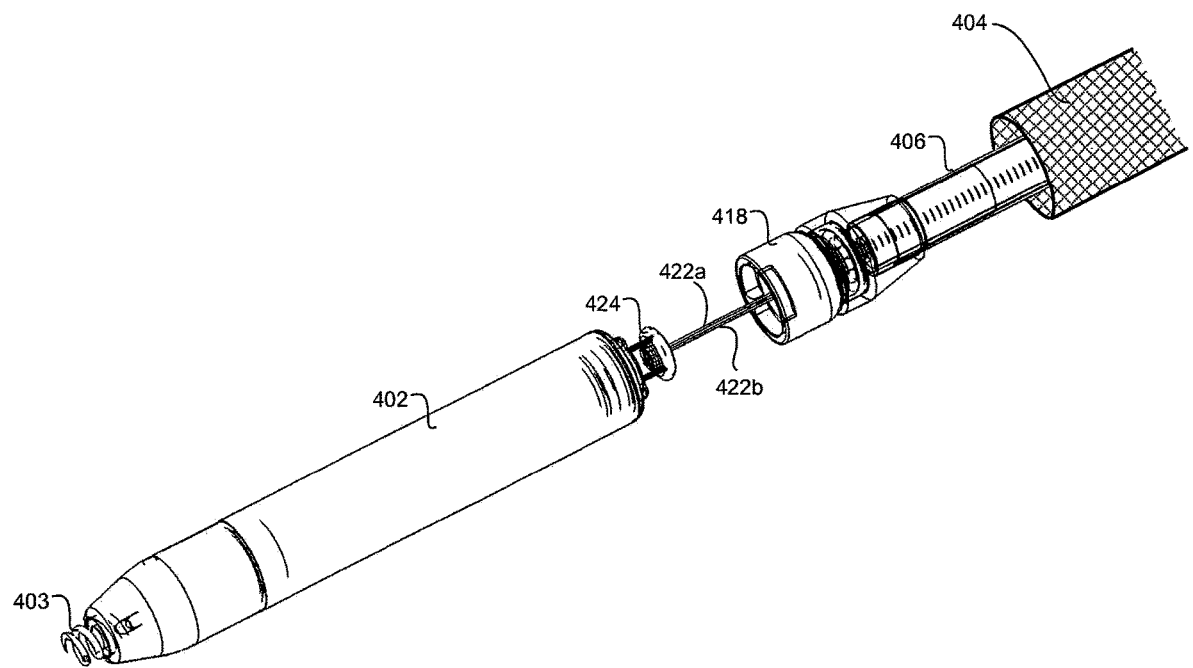

To connect the delivery catheter to the pacemaker, the length of tethers 422a and 422b, and thus the position of distal features 426a and 426b, can be adjusted so that distal features 426a and 426b are not aligned in a side by side configuration (e.g., the un-aligned configuration shown in FIGS. 4A-4B). When the tethers and distal features are in this un-aligned configuration, the cross sectional diameter of the distal features is reduced since the distal features are not positioned side by side. The tether distal features 426a and 426b can then be advanced in this un-aligned configuration through hole 428 of attachment feature 424, as shown in FIGS. 4D-4F. In this embodiment, the diameter of hole 428 should be sufficiently large enough to allow the distal features 426a and 426b of tethers 422a and 422b to pass when in the un-aligned configuration. Upon passing the distal features through the hole 428, the length of the tethers can then be adjusted to align the distal features in the side by side configuration (e.g., as shown in FIGS. 4C and 4E). When the distal features are positioned side by side, the combined cross sectional diameter of the distal features becomes larger than the diameter of hole 428, which essentially locks the tethers and distal features in the attachment feature 424 by preventing the distal features from being able to pass proximally through the hole 428.

Figure 4G:
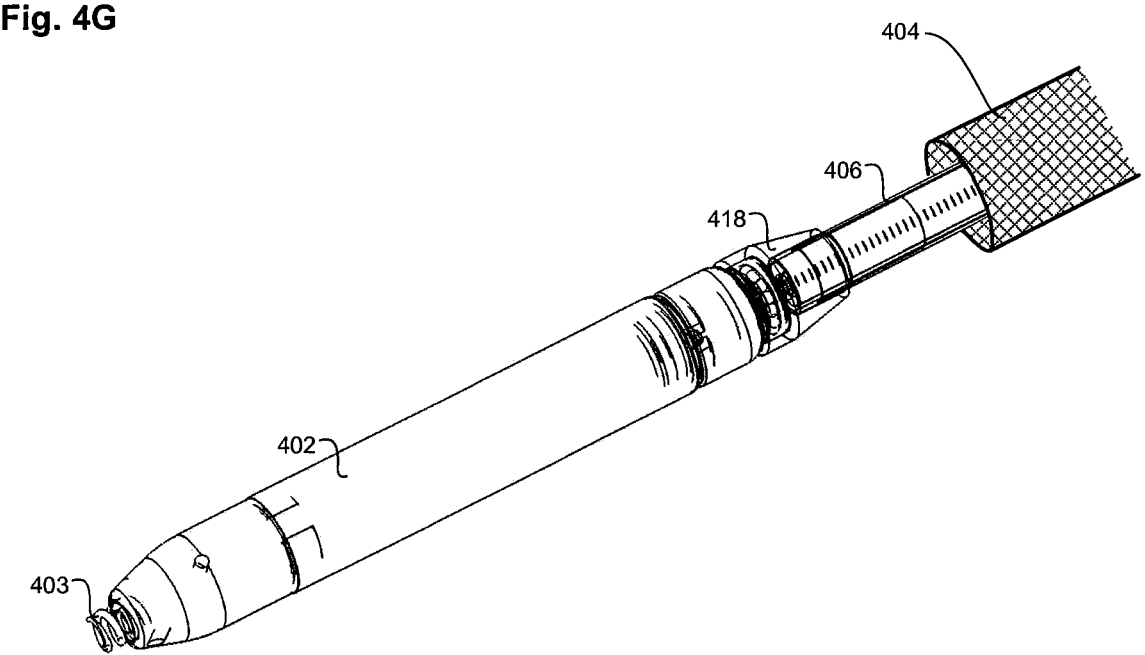

Still referring to FIGS. 4C and 4D, the docking cap 418, which is supported on the distal end catheter shaft 406 of the delivery catheter, can include a torque slot 430 (shown in FIG. 4C) sized and configured to mate with a torque key 432 (shown in FIG. 4D) disposed on a proximal end of the pacemaker. The torque slot 430 is located in docking cap 418 and coupled to a torque shaft 431, which runs the length of catheter shaft 406 of the delivery catheter to extend into the handle (not shown). In FIGS. 4C and 4D, torque key 432 is shown as a "male" key on the proximal end of pacemaker 402, and torque slot 430 is shown as a "female" key, but it should be understood that in other embodiments, the "male" key can be located on the attachment feature 418, and the "female" key can be disposed on the pacemaker. It should also be appreciated that key 432 and slot 430 can comprise any number of shapes, such as square, rectangle, triangle, pentagon, hexagon, cross, "X", etc., so long as key 432 fits within torque slot 430 for the transfer of rotation torque between the two elements 430, 432. Once the tethers are locked within the attachment feature, the tethers can be pulled proximally to pull attachment feature 424 and the pacemaker towards the catheter and to attach the pacemaker to the delivery catheter, thereby engaging torque slot 430 with torque key 432 (as shown in FIG. 4G).

Figure 5A:
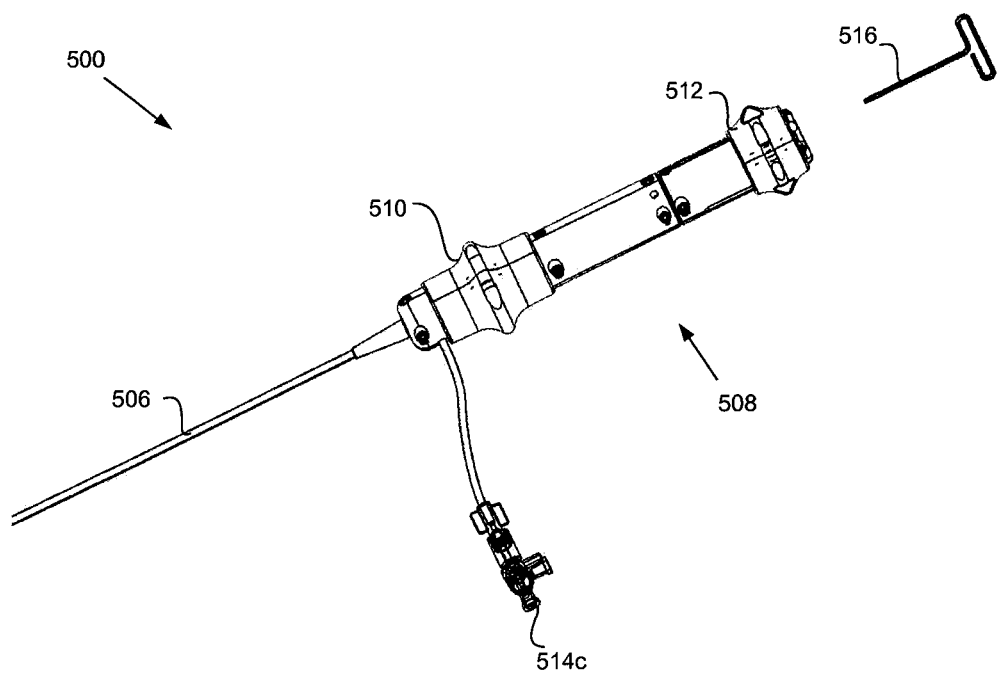
FIGS. 5A-5D are various views of a catheter handle and tether key.
Figure 5B:
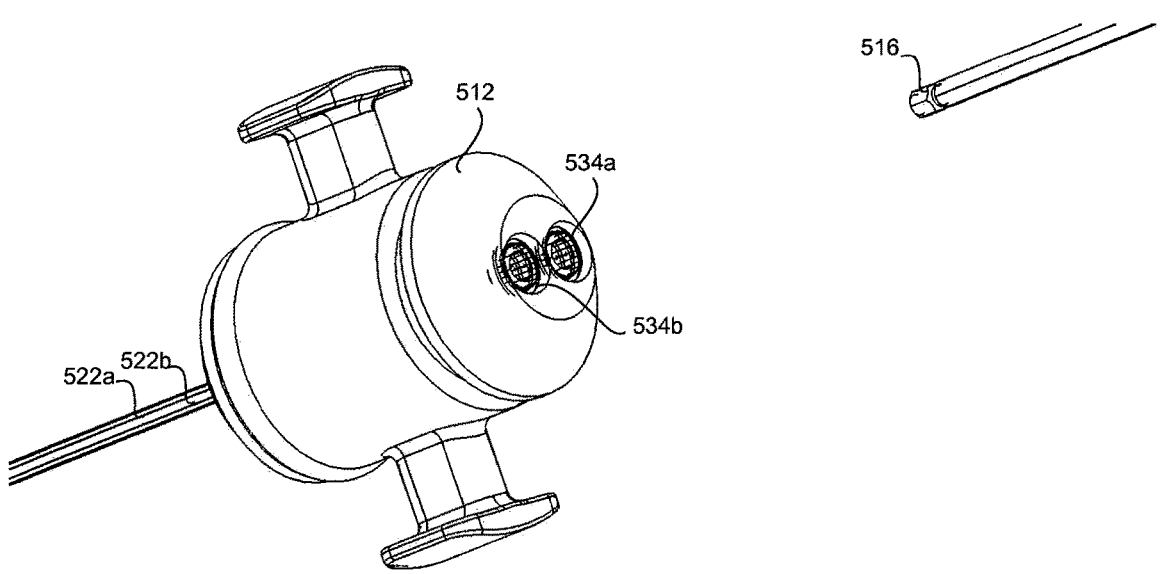
Figure 5C:
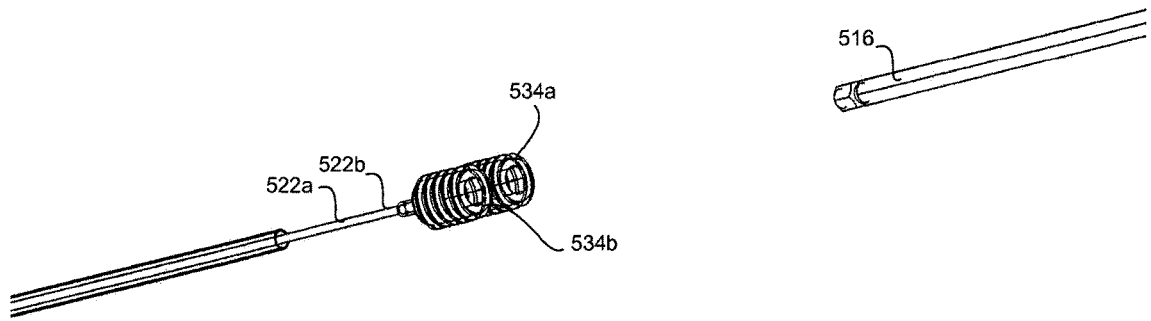

FIGS. 5A-5D are close-up views of handle 508 of delivery system 500. In FIG. 5A, handle 508 includes deflection knob 510, tether shuttle 512, tether adjustment feature 516, and flush port 514c. As described above, deflection knob 510 provides for steering and guidance of the catheter during implantation and/or removal of the pacemaker. The flush port 514c can be used to flush saline or other fluids through the catheter. Referring now to FIGS. 5B and 5C, tether adjustment feature 516 can be configured to adjust the length of tethers 522a and 522b that extends distally outwards from the delivery catheter, causing the distal features (not shown) to be in either a side by side "locked" configuration or an un-aligned "unlocked" configuration.

Figure 5D:
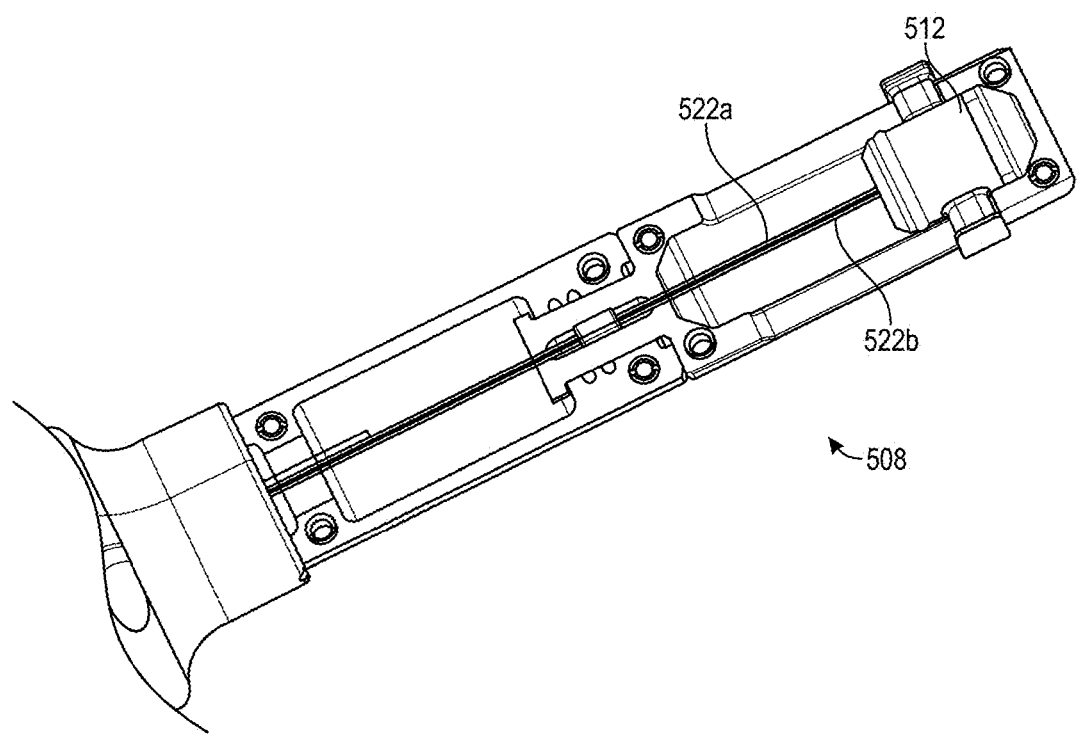

The tether adjustment feature can comprise an Allen wrench or any other suitable key, and can be configured to mate with and engage proximal keys 534a and 534b of tethers 522a and 522b, respectively, which are disposed within shuttle 512. In another embodiment, the tether adjustment feature can comprise knobs or dials on the handle itself, and a user can simply turn the knobs or dials to adjust the length of the tethers. The shuttle can be inserted into handle 508, as shown in FIG. 5D. The proximal keys 534a and 534b of tethers 522a and 522b are shown without shuttle 536 in FIG. 5C for ease of illustration. Rotation of tether adjustment feature 516 causes proximal keys 534a and/or 534b to move distally or proximally within shuttle 512, which therefore changes the length of tethers 522a and/or 522b extending distally from the delivery catheter. Thus, the tether key can be used to either align the distal features of the tethers in a side by side (e.g., locked) configuration, or alternatively, to place the distal features of the tethers in an un-aligned (e.g., unlocked configuration), permitting docking and locking of the pacemaker to the delivery catheter.

Referring back to FIGS. 4D-4G and 5A, it can now be understood how the pacemakers described herein can be delivered and attached to tissue, and then released from the delivery system. In FIGS. 4D-4F, tethers 422a and 422b can be inserted in an "unlocked" or un-aligned configuration into hole 428 of attachment feature 424. The distal features of the tethers can then be aligned so as to lock the distal features in the attachment feature. Referring to FIG. 5A, tether shuttle 512 can then be pulled proximally to cause the tethers to move proximally, thereby docking the pacemaker against the delivery catheter (as shown in FIG. 4G). When the pacemaker is docked against the delivery catheter, torque key 432 of the pacemaker (shown in FIG. 4D) fits within and is mated to torque slot 430 of the delivery catheter (shown in FIG. 4C).

Referring to FIG. 5A, tether shuttle 512 of handle 508 can then be rotated, which rotates torque shaft 431 (shown in FIG. 4C) within the delivery catheter and applies torque to torque slot 430, and thus to torque key 432 on the pacemaker. By rotating the shuttle, and thus the torque shaft, the delivery catheter applies torque to the pacemaker to screw the fixation helix of the pacemaker into tissue. Once the fixation helix is fully inserted into tissue, the tethers can be placed into an un-aligned or "unlocked" configuration with tether adjustment feature 516, allowing the tethers and distal features to be removed from the attachment feature of the pacemaker. Once the delivery catheter is disengaged from the pacemaker, the catheter can be removed from the patient, leaving the pacemaker in place at the target tissue.

Figure 6A:
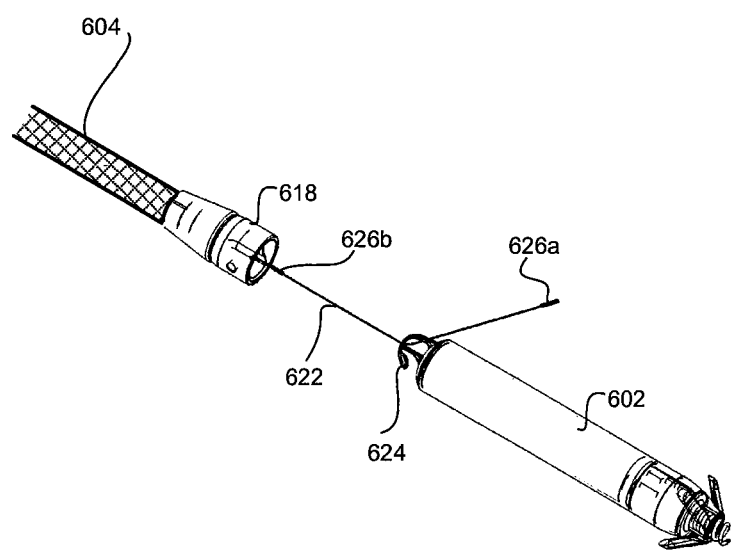
FIGS. 6A-6B are an alternate embodiment of a delivery system having a single tether.
Figure 6B:
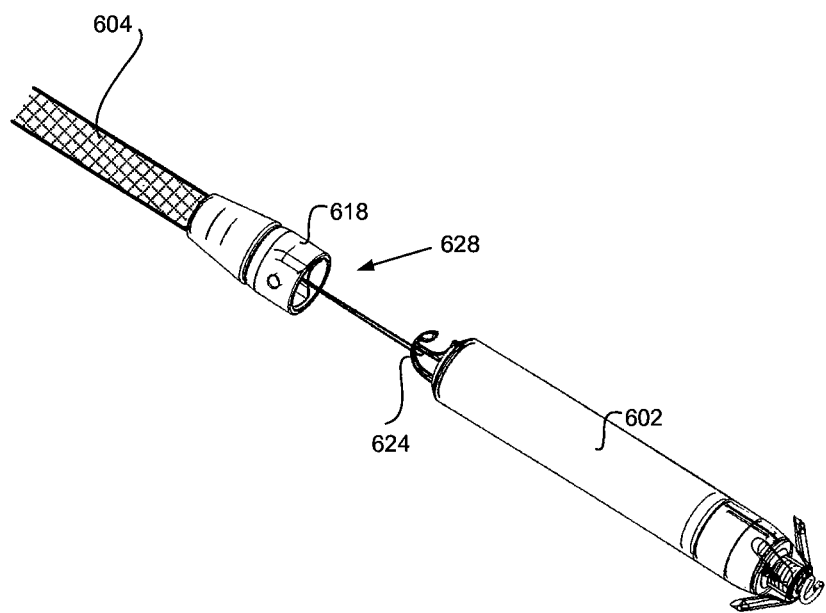

FIGS. 6A and 6B illustrate an alternate embodiment for attaching a delivery catheter to a pacemaker. The embodiment shown in FIGS. 6A and 6B employs a similar concept to that described above. However, instead of using two tethers, as described above, the embodiment of FIGS. 6A and 6B utilizes a single tether 622, having both a distal feature 626a and a proximal feature 626b. In the embodiment of FIGS. 6A and 6B, the tether 622 can comprise a shape memory alloy, such as nitinol, and can include a pre-bent or pre-biased shape. This pre-biased shape can allow the distal feature 626a of the tether to naturally bias outwards, as shown in FIG. 6A.

To attach the pacemaker 602 to the delivery catheter, as shown in FIG. 6A, the distal feature 626a of tether 622 can be threaded through attachment feature 624 of pacemaker 602. Once the tether is threaded through the attachment feature, the tether can be folded back against itself, so that distal feature 626a is adjacent to, but not directly beside proximal feature 626b. The distal and proximal features should be aligned in an un-aligned or "unlocked" configuration, as described above in the two-tether embodiments. This configuration allows the distal and proximal features to be inserted into hole 628 of docking cap 618, as shown in FIG. 6B. Once the distal and proximal features are advanced past the hole 628, an interior chamber (not shown) in the catheter opens up to a diameter larger than the diameter of the hole 628. This interior chamber has a diameter large enough to accommodate both the distal and proximal features in a side by side or "locked" configuration. Thus, the length of the tether can be adjusted to align the distal and proximal features in the side by side configuration, causing the combined cross sectional diameter of the distal and proximal features to be larger than the diameter of hole 628. The result is the locking of tether 622 within the delivery catheter.

Other features of the embodiment of FIGS. 6A-6B can be the same as described above, such as the torque keys, slots, and shafts that allow the delivery catheter to apply rotational torque to the pacemaker to screw it into tissue. Further, atraumatic pacemaker sheath 604 can be as described above to facilitate the safe delivery of leadless pacemaker 602 to the implantation site.

As for additional details pertinent to the present disclosure, materials and manufacturing techniques may be employed as within the level of those with skill in the relevant art. The same may hold true with respect to method-based aspects of the present disclosure in terms of additional acts commonly or logically employed. Also, it is contemplated that any optional feature of the systems and methods disclosure herein may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this present disclosure belongs. The breadth of the present disclosure is not to be limited by the subject specification, but rather only by the plain meaning of the claim terms employed.

What is claimed is:

1. A delivery catheter, comprising:
   a guide sheath including
      a tubular body having a lumen and a distal end,
      a sleeve extending distally from the distal end, the sleeve having a dual-wall construction, and
      a liner layer supported loosely on the sleeve, wherein the liner layer includes a rounded end, wherein the liner layer has a backward fold at the rounded end; and
   a catheter shaft extending through the lumen from a handle to a docking cap, wherein the catheter shaft and the guide sheath are longitudinally displaceable relative to each other.

2. The delivery catheter of claim 1, wherein the dual-wall construction includes at least one of a braided, woven, or mesh construction defining a volume coaxial with the lumen.

3. The delivery catheter of claim 1 further comprising one or more sutures attaching the liner layer to the sleeve.

4. The delivery catheter of claim 1 further comprising a radiopaque marker coupled to the liner layer.

5. The delivery catheter of claim 4, wherein the rounded end of the sleeve extends around the radiopaque marker.

6. The delivery catheter of claim 1, wherein, when the sleeve slides over the docking cap, the sleeve expands against an inner surface of the liner layer.

7. The delivery catheter of claim 1, wherein the docking cap includes a slot configured to receive an attachment feature of a biostimulator to dock the biostimulator against the delivery catheter.

8. A biostimulator system, comprising:
   a biostimulator; and
   a delivery catheter comprising:
      a guide sheath including
         a tubular body having a lumen and a distal end,
         a sleeve extending distally from the distal end, the sleeve having a dual-wall construction,
         a liner layer supported loosely on the sleeve, wherein the liner layer includes a rounded end, and wherein the liner layer has a backward fold at the rounded end, and
      a catheter shaft extending through the lumen from a docking cap to a handle, wherein the catheter shaft and the guide sheath are longitudinally displaceable relative to each other.

9. The biostimulator system of claim 8, wherein the dual-wall construction includes at least one of a braided, woven, or mesh construction defining a volume coaxial with the lumen.

10. The biostimulator system of claim 8 further comprising one or more sutures attaching the liner layer to the sleeve.

11. The biostimulator system of claim 8 further comprising a radiopaque marker coupled to the liner layer.

12. The biostimulator system of claim 11, wherein the rounded end of the sleeve extends around the radiopaque marker.

13. The biostimulator system of claim 8, wherein, when the sleeve slides over the biostimulator, the sleeve expands against an inner surface of the liner layer.

14. The biostimulator system of claim 8, wherein the docking cap includes a slot configured to receive an attachment feature of a biostimulator to dock the biostimulator against the delivery catheter.

\* \* \* \* \*